US012605107B1

(12) United States Patent
    Arruda

(10) Patent No.: US 12,605,107 B1
(45) Date of Patent: Apr. 21, 2026

(54) MULTI-USE ELECTROENCEPHALOGRAM SYSTEM AND METHOD

(71) Applicant: James Edward Arruda, Milton, FL (US)

(72) Inventor: James Edward Arruda, Milton, FL (US)

( * ) Notice: Subject to any disclaimer, the term of this patent is extended or adjusted under 35 U.S.C. 154(b) by 846 days.

(21) Appl. No.: 17/847,649

(22) Filed: Jun. 23, 2022

Related U.S. Application Data

(60) Provisional application No. 63/214,851, filed on Jun. 25, 2021.

(51) Int. Cl.
    | | |
    |---|---|
    | *A61B 5/00* | (2006.01) |
    | *A61B 5/256* | (2021.01) |
    | *A61B 5/291* | (2021.01) |
    | *A61B 5/30* | (2021.01) |
    | *A61B 5/378* | (2021.01) |
    | *A61B 5/384* | (2021.01) |

(52) U.S. Cl.
    CPC .......... *A61B 5/4088* (2013.01); *A61B 5/0006* (2013.01); *A61B 5/0022* (2013.01); *A61B 5/256* (2021.01); *A61B 5/291* (2021.01); *A61B 5/30* (2021.01); *A61B 5/378* (2021.01); *A61B 5/384* (2021.01); *A61B 5/6803* (2013.01)

(58) Field of Classification Search
    None
    See application file for complete search history.

(56) References Cited

U.S. PATENT DOCUMENTS

2013/0060125 A1* 3/2013 Zeman ................... A61B 5/374
                                                        600/409

OTHER PUBLICATIONS

Arruda, James E. et al., The effect of wavelength on the variability of the flash visual evoked potential P2: A potential biomarker for mild cognitive impairment and Alzheimer's dementia, 2021, Elsevier, International Journal of Psychophysiology 164 p. 23-29 (Year : 2021).*
Pojda-Wilczek, Dorota et al., Flash visual evoked potentials (FVEP) in various stimulation conditions, 2018, Springer, Doc Ophthalmol 138 p. 35-42 (Year: 2018).*

* cited by examiner

*Primary Examiner* — Aurelie H Tu
(74) *Attorney, Agent, or Firm* — J. Nevin Shaffer, Jr.

(57) ABSTRACT

A multi-use electroencephalogram (EEG) system and method consists of a strobe where the strobe is adjustable to produce single and multiple strobe flashes. An EEG device connected with the strobe configured for time-locking an EEG recording with the strobe where the EEG device measures patient flash visual evoked potential (FVEP) response to the strobe flashes and a controller connected with the strobe and the EEG device where the controller operates the strobe to produce one single strobe flash condition followed by a double strobe flash condition employing various interstimulus intervals in a complete counterbalanced order.

18 Claims, 3 Drawing Sheets

MULTI-USE ELECTROENCEPHALOGRAM SYSTEM AND METHOD

CROSS REFERENCE TO RELATED APPLICATION

This application claims the benefit of previously filed U.S. provisional patent application No. 63/214,851 filed Jun. 25, 2022 for a "Multi-Use Electroencephlaogram System and Method". The Applicant hereby claims the benefit of this provisional application under 35 U.S.C. § 119. The entire content of this provisional application is incorporated herein by this reference.

FIELD OF THE DISCLOSURE

The present invention pertains to a multi-use electroencephalogram (EEG) system that is capable of detecting cognitive impairment. Comprising the EEG system is a strobe, defined here as either a stroboscope or goggles, where the strobe is adjustable to produce single- and/or multiple-strobe flashes at various rates and of various duration, intensities, and colors, and an EEG acquisition unit that is capable of measuring and analyzing the time-locked EEG related to the presentation of the various strobe flashes. Of particular interest is the time-locked EEG that is commonly referred to as the flash visual evoked potential P2 (FVEP-P2), which is exhibited by the visual cortex in response to repeated strobe flashes. It is this biomarker that may prove useful in the early diagnosis of amnestic mild cognitive impairment (aMCI) and Alzheimer's dementia (AD).

That is, the present invention, in broadest terms, consists of a strobe where the strobe is adjustable to produce both single and multiple strobe flashes and an EEG device designed to record time-locked EEG in response to each strobe flash. Furthermore, the EEG device is capable of averaging the time-locked EEG responses, creating a graphic and quantitative representation of the FVEP, including the P1, N2, and P2. The P1 is a component of the evoked response that is thought to be related to the arrival of the strobe flash information in the sparsely cholinergic primary visual cortex. The N1 is believed to mark a transition between the arrival of the strobe flash information at the primary visual cortex and the arrival of the strobe flash information at the heavily cholinergic associational visual cortex. Characteristics of the P1, N2, and P2, including latency and amplitude, are then used to evaluate individuals who are suspected of having aMCI. Indeed, it is the comparison of the response produced by the single and the multiple strobe flash conditions that prove diagnostic, as multiple flashes place a demand on the visual system of those with aMCI that adversely affect the FVEP response. The EEG device is not only be able to record the time-locked EEG, it is also capable of analyzing the characteristics of the FVEP waveforms, and producing numerical indices that assist in the evaluation of dementia due to aMCI. Cloud based computing will also play a role, as the data obtained will be used to update a database that will allow for descriptive reports to be produced for each user.

BACKGROUND OF THE INVENTION

The scientific and medical communities have been attempting to develop a biomarker capable of detecting the early neuropathological changes associated with amnestic aMCI and AD. It is the belief of both communities that the early detection of aMCI and AD might lead to more effective treatments. Unfortunately, the biomarkers currently available are expensive and invasive, which inhibits their broader use in clinics trials, clinics, and other health delivery centers. Such methods include the analysis of cerebral spinal fluid (CSF), brain metabolism (positron emissions tomography or "PET"), and neuropsychological testing. The latter of which is often confounded by a lack of test administrator expertise and diminished patient motivation. Not surprisingly, a need exists for the development of a brief, non-invasive, and inexpensive biomarker that is both sensitive and specific to the neuropathological changes that are often associated with aMCI and AD: declines in acetylcholine, a neurotransmitter. The object of this invention is to provide an efficient, non-invasive, and inexpensive method for detecting the early neuropathological changes associated with aMCI and AD using a neurophysiological biomarker related to EEG.

SUMMARY

Accordingly, a multi-use EEG system, according to one embodiment of the invention, consists of a strobe, where the strobe is adjustable to produce single and multiple double strobe flashes of various durations, intensities, and colors; an EEG acquisition unit comprised, for example only and not by limitation, of a preamplifier, an amplifier, and an electrode cap capable of recording both continuous EEG and evoked/event related potentials, including the FVEP; and an analysis unit capable of analyzing continuous (e.g., spectral analyzed) and evoked/event related potentials, including the FVEP; and a unit capable of cloud-based computing that would allow for the uploading of recorded data and the downloading of reports.

Event related potentials, as is known in the art, are not flash visual evoked potentials (FVEPs) but are time locked brain responses to cognitive stimuli such as words and language. VEPs are time-locked brain responses to visual stimuli such as patterns versus light flashes. FVEPs are based solely on a strobe flash and are evoked, automatically produced, by the extrastriate cortex once the visual information associated with the strobe is perceived.

Again, in broadest terms, the invention consists of a strobe where the strobe is adjustable to produce both single and multiple strobe flashes and an EEG device designed to record time-locked EEG in response to each strobe flash. Furthermore, the EEG device averages the time-locked EEG responses, creating a graphic and quantitative representation of the FVEP, including the P1, N2, and P2 components of the waveform. Characteristics of the P1, N2, and P2, including latency and amplitude, are then be used to evaluate individuals who are suspected of having aMCI. Indeed, it is the comparison of the response produced by the single and the multiple strobe flash conditions that prove diagnostic, as multiple flashes place a demand on the visual system of those with aMCI that adversely affects the FVEP response. The EEG device is not only able to record the time-locked EEG, it is also configured to analyze the characteristics of the FVEP waveforms and produce numerical indices that will assist in the evaluation of dementia due to aMCI. Cloud based computing will also play a role, as the data obtained will be used to update a database that will allow for descriptive reports to be produced for each user.

All terms used herein are given their common meaning as known to those of ordinary skill in the art as with "strobe," "EEG," "acquisition," "analysis," and "multi-use EEG system." For clarity, "multi-use EEG system" identifies a machine device, wireless or wired, configured for use in operating other devices and for receiving and processing and transmitting data from other devices and to other devices such as a computer for example only and not by way of limitation. Likewise, for clarity, "controller" identifies a machine device, wireless or wired, configured for use in operating other devices and for receiving and processing and transmitting data from other devices and to other devices such as a computer for example only and not by way of limitation.

According to one embodiment, a multi-use electroencephalogram (EEG) system consists of a strobe where the strobe is adjustable to produce single and multiple strobe flashes. An EEG device connected with the strobe configured for time-locking an EEG recording with the strobe where the EEG device measures patient flash visual evoked potential (FVEP) response to the strobe flashes and a controller connected with the strobe and the EEG device where the controller operates the strobe to produce one single strobe flash condition followed by a double strobe flash condition employing various interstimulus intervals in a complete counterbalanced order.

In one aspect, the strobe is configured in a goggle with two lenses with more than one light emitting diode in each lens.

In one aspect, the controller operates the strobe to produce one single strobe flash condition followed by more than one double strobe flash condition in a complete counterbalanced order. In one aspect, the double strobe flash conditions are produced with varying interstimulus intervals, durations, intensities, colors, and frequencies.

In another aspect, the strobe produces strobe flashes selected from a group of strobe flashes consisting of: colored strobe flashes, strobe flashes of variable duration, strobe flashes of variable brightness, strobe flashes of variable frequency, and double strobe flashes of variable interstimulus intervals.

According to another embodiment, a multi-use electroencephalogram (EEG) device consists of a strobe where the strobe is adjustable to produce single and multiple strobe flashes of various durations, intensities, colors, and frequencies. A multi-use EEG acquisition system connected with the strobe configured for recording both continuous and time-locked EEG, including flash visual evoked potential (FVEP)- and event-related potentials and a multi-use EEG analysis system, connected with the multi-use acquisition system, configured for analyzing both continuous and time-locked EEG, including FVEP- and event-related potentials (e.g., FVEP) where the multi-use EEG analysis system is configured for cloud-based computing enabling uploading of recordings and the downloading of descriptive reports.

In one aspect, the strobe is configured in a goggle with two lenses with more than one light emitting diode in each lens.

In another aspect, the multi-use EEG system operates the strobe to produce one single strobe flash condition followed by more than one double strobe flash condition in a complete counterbalanced order. In one aspect, the double strobe flash conditions are produced with varying interstimulus intervals, durations, intensities, colors, and frequencies.

In a further aspect, the strobe produces strobe flashes selected from a group of strobe flashes consisting of: colored strobe flashes, strobe flashes of variable duration, strobe flashes of variable brightness, strobe flashes of variable frequency, and double strobe flashes of variable interstimulus intervals.

According to another embodiment, a multi-use electroencephalogram (EEG) method consists of:

a. providing a strobe where the strobe is adjustable to produce single and multiple strobe flashes;

an electroencephalogram (EEG) device configured for time-locking with the strobe where the EEG device measures patient flash visual evoked potential (FVEP) response to the strobe flashes and a controller connected with the strobe and the EEG device where the controller operates the strobe to produce one single strobe flash condition followed by one double strobe flash condition; and b. activating the controller to operate the strobe such that the EEG obtains FVEP responses.

In one aspect, the strobe is configured in a goggle with two lenses with more than one light emitting diode in each lens.

In another aspect, the controller operates the strobe to produce one single strobe flash condition followed by one double strobe flash condition in a complete counterbalanced order.

In one aspect, the controller operates the strobe to produce one single strobe flash condition followed by more than one double strobe flash condition in a complete counterbalanced order.

In one aspect, the strobe produces double flashes with varying time intervals and in one aspect, the varying time intervals are in a range from 80 ms to 500 ms.

In another aspect, the strobe produces strobe flashes selected from a group of strobe flashes consisting of: colored strobe flashes, strobe flashes of variable duration, strobe flashes of variable brightness, strobe flashes of variable frequency, and double strobe flashes of variable interstimulus intervals.

In one aspect, the controller operates the strobe to produce one single strobe flash condition followed by one double strobe flash condition in a complete counterbalanced order. In another aspect, the double strobe flash conditions are produced with varying interstimulus intervals, durations, intensities, colors, and frequencies.

In a further aspect, the strobe produces strobe flashes selected from a group of strobe flashes consisting of: colored strobe flashes, strobe flashes of variable duration, strobe flashes of variable brightness, strobe flashes of variable frequency, and double strobe flashes of variable interstimulus intervals.

DESCRIPTION OF THE DRAWINGS

Other objects, features and advantages of the present invention will become more fully apparent from the following detailed description of the preferred embodiment, the appended claims and the accompanying drawings in which:

DETAILED DESCRIPTION OF EMBODIMENTS

Figure 1:
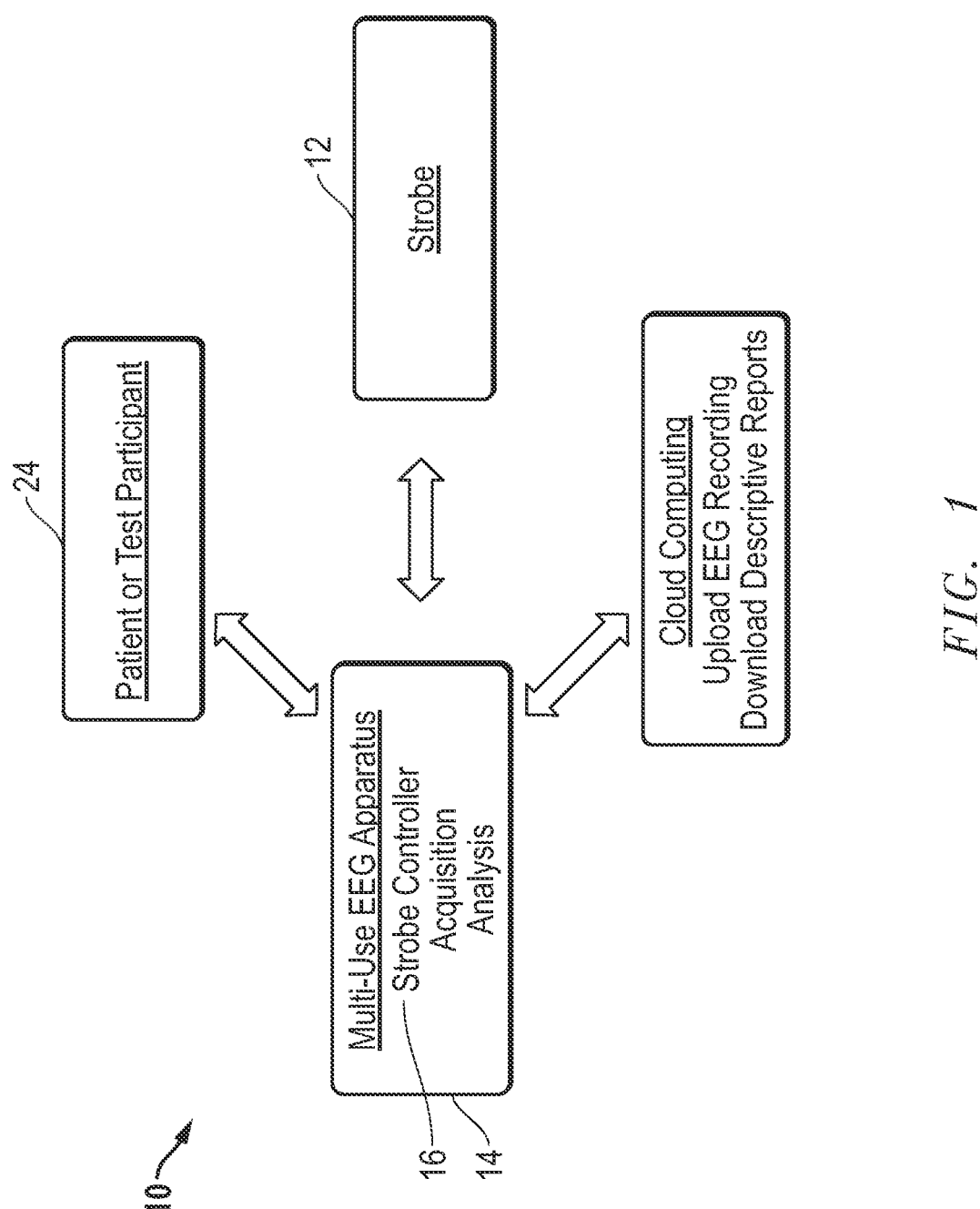
FIG. 1 is a schematic diagram of the multi-use electroencephalogram (EEG) system of the present invention.

Before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the invention be regarded as including equivalent constructions to those described herein insofar as they do not depart from the spirit and scope of the present invention.

For example, the specific sequence of the described process may be altered so that certain processes are conducted in parallel or independent, with other processes, to the extent that the processes are not dependent upon each other. Thus, the specific order of steps described herein is not to be considered implying a specific sequence of steps to perform the process. In alternative embodiments, one or more process steps may be implemented by a user assisted process and/or manually. Other alterations or modifications of the above processes are also contemplated. For example, further insubstantial approximations of the process and/or algorithms are also considered within the scope of the processes described herein.

In addition, features illustrated or described as part of one embodiment can be used on other embodiments to yield a still further embodiment. Additionally, certain features may be interchanged with similar devices or features not mentioned yet which perform the same or similar functions. It is therefore intended that such modifications and variations are included within the totality of the present invention.

It should also be noted that a plurality of hardware- and software-based devices, as well as a plurality of different structural components, may be utilized to implement the invention. Furthermore, and as described in subsequent paragraphs, the specific configurations illustrated in the drawings are intended to exemplify embodiments of the invention and that other alternative configurations are possible.

Figure 2:
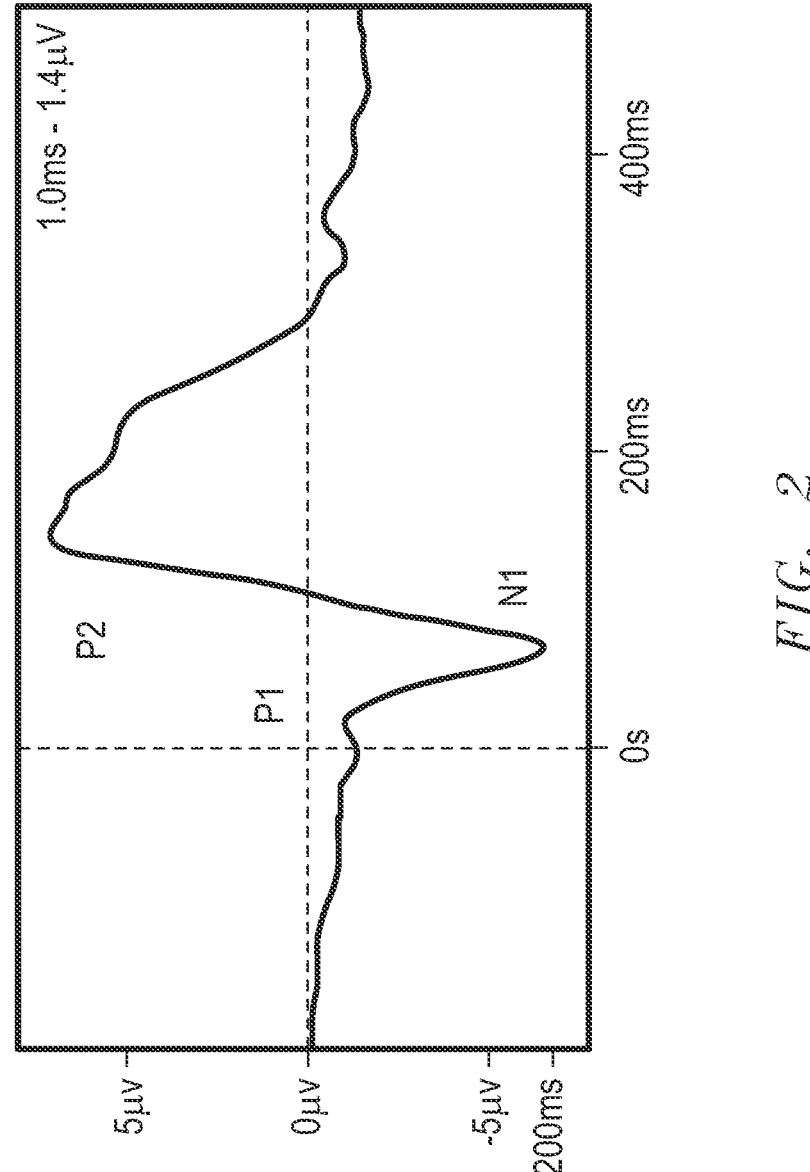
FIG. 2 shows the FVEP-P2, which is the second positive component of a VEP waveform produced after the presentation of repeated strobe flashes. The latency of the P2 is selectively delayed in patients diagnosed with either aMCI or AD.
Figure 3:
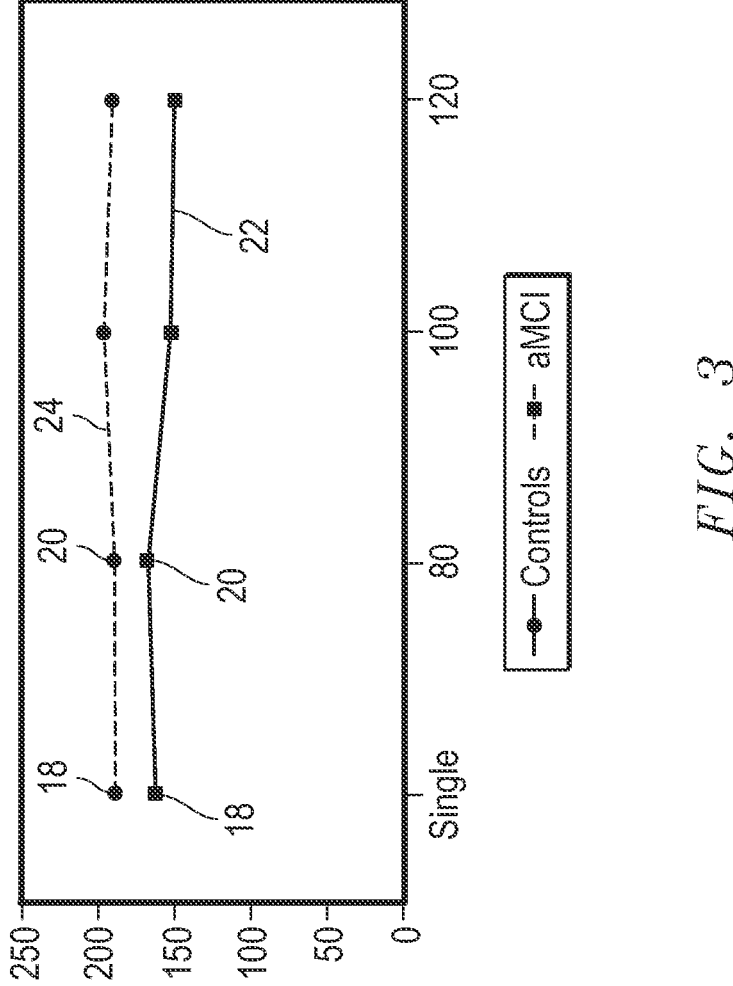
FIG. 3 is a chart illustrating the results of the invention in a sample of aMCI patients and age equivalent controls. The latencies associated with the sample of aMCI patients increase as a function of the double-flash conditions and that the P2 latencies associated with age equivalent controls appear to return to baseline as the ISIs associated with the double-flash condition increases.

One embodiment of the present invention is illustrated by way of example in FIGS. 1, 2, and 3. Referring now to FIG. 1, the multi-use electroencephalogram (EEG) system 10, according to one embodiment, includes a strobe 10, where the strobe 10 is adjustable to produce single or multiple strobe flash conditions of various durations, intensities, and colors. Strobes, including those that are LED based or gas based, are known in the art and function to produce flashes of light and are not described more fully hereafter. An EEG device 14 is connected with the strobe 12 and is configured for time-locking an EEG recording with the strobe 12 where the EEG device 14 measures patient flash visual evoked potential (FVEP) response to the strobe flashes.

A controller 16 is connected with the strobe 12 and the EEG device 14 where the controller 16 operates the strobe 12 to produce one single strobe flash condition followed by a double strobe flash condition employing various interstimulus intervals in a complete counterbalanced order.

The multi-use EEG system 10 is capable of recording and analyzing EEG for other purposes, including spectral and component analysis.

The multi-use EEG system 10 is capable of controlling the presentation of strobe flashes, as well as the acquisition and analysis of EEG. The multi-use EEG system 10 may also come with a preamplifier, amplifier, and electrode cap as may be determined useful.

One capability of the multi-use EEG system 10 is the provision of a novel FVEP-P2 assessment procedure that produces a neurophysiological marker that is capable of detecting the early neuropathological changes associated with aMCI and AD. As can be seen in FIG. 2, the FVEP-P2, which is the second positive component of a VEP waveform produced after the presentation of repeated strobe flashes. VEP waveforms are produced by averaging time-locked EEG. In this case, the EEG acquisition is time-locked to repeated strobe flashes and the response of the brain (i.e., visual cholinergic cortex) to the strobe flash is recorded in milliseconds.

The latency of the FVEP-P2 has proven to be a tenable biomarker for the detection of aMCI and AD given that it has been demonstrated to be selectively delayed in those diagnosed with both disorders. Unlike the FVEP-P1, whose latency is associated with processing from the retina to the primary visual cortex, the latency of the P2 is associated with processing between the primary visual cortex and associational visual cortex, which is highly dependent on ascending cholinergic projections. The basal nucleus, a subcortical structure that is the primary source for ascending cholinergic projections, is often destroyed in aMCI and AD, decreasing arousal within the cortex and decreasing the speed of information processing. Patients diagnosed as having aMCI or AD typically exhibit a selective delay in the latency of the P2 compared to healthy controls. The P2 delay not only mirrors the cholinergic deterioration that is characteristic of AD, it also increases with the onset and course of AD and is not associated with other forms of dementia.

Referring to FIG. 3, a single flash condition 18 is compared with a double flash condition 20 and compared with a control group 22 versus the patient 24. The present invention provides a novel double-flash (assessment) procedure that improves upon the traditional single flash paradigm by including a strobe-based challenge to the condition that appears to further separate patients and age equivalent controls in terms of their P2 latency.

The FVEP-P2 assessment procedure according to the present invention is configured to administer several FVEP conditions in a complete counterbalanced order (ABBA). This process will assist with the carry-over effects associated with practice and allows examination of individual scores unconfounded by fatigue. As an example, if fifty strobe flashes for conditions B and A were presented, the preferred method according to the present invention is to reverse the order and present fifty additional strobe flashes for conditions A and B. The presentation order and condition characteristics would be unknown to the patient because the conditions would be presented in succession and without breaks. The averaging of the waveforms in this example would come after each entire recording and be based on the 100 predestinations comprising each of the conditions (A and B). Preferably, each strobe presentation would come at an interval of approximately 1.5 s.

To extend the example further, if the system is used, according to one embodiment, to present a single flash condition and then additional double-flash conditions (e.g., Single Flash Condition and 370 ISI Double Flash Condition) in a single assessment, the results of the assessment would be a clinical profile for each patient, that when compared to age equivalent controls, would allow a clinician or a researcher to examine a pattern of performance an individual experienced, including his or her recovery from each cholinergic challenge. Again, ISI refers to the interstimulus interval between strobe flashes.

As can be seen in FIG. 3, the difference in FVEP-P2 delay between age equivalent controls 22 and patients/test subjects 24 diagnosed with aMCI increased as a function of the double-flash challenge. Aspects of the cognitive impairment detection process may also be cloud-based so that a user could continue to collect clinical and control data, as well as neuropsychological and demographic data, while also providing the user (clinician/researcher) with a norm-referenced description of a patient's test performance.

For flexibility, other FVEP-P2 parameters may be programmed into the system (or module), including a choice of strobe color, strobe duration, strobe intensity, and strobe frequency. However, the FVEP-P2 assessment by the present invention would, preferably, be standardized and automatically programmed into the multi-use EEG system 10 to provide a "plug-and-play" interface.

The current device is based on common BIOPAC technology (amplifiers, stimulators, etc.), but scripting has been added to perform what we, through consensus, believed would be as brief an assessment as possible (5 minutes).

Currently, the assessment involves goggles that produce red light using 10 LEDs (5 per eye) and the goggles are controlled by the aforementioned scripting and devices. As used herein, "goggles" describes a device covering a user's eyes, either two lens or one as are known and not described more fully hereafter. The test conditions are a single- and a double-flash (interstimulus interval of 370 milliseconds) conditions that have been counterbalanced in order of presentation to spread any carry-over effect between them. Hence, the order of presentation is as follows: 1) 50 trials of single-flash, 2) 50 trials of double-flash, 3 50 trials of double-flash, and 4) 50 trials of single-flash.

Further, once administered, the two single-flash and the two double-flash conditions are combined to create one 100 trial single-flash condition and one 100 trial double-flash condition. The 100 trials of each condition are then averaged to create the flash visual evoked potential waveform, of which the P1, N1, and P2 components are most notable. Of the three components, the P2 is the most important, given that it is believed to be sensitive to cholinergic functioning.

Measures that pertain to the P2 include 1) the P2's single-flash latency and amplitude and the P2's double-flash latencies and amplitudes. The P2 associated with the first of the two flashes of the double-flash condition is used to validate the P2 obtained from the single-flash condition and the P2 associated with the second of the two flashes of the double-flash condition is used to assess clinical status of an individual, given that it is considered to be the "challenge" condition.

Latency:

In theory, according to the present invention, the latency associated with the P2 produced by the single-flash condition should be delayed when compared to individuals with mild cognitive impairment—this could be diagnostic. The same would be true of the first of two P2s obtained from the double-flash condition. However, the delay associated with the second P2 of the double-flash condition (the challenge) should be even more delayed than in the single flash condition, given the challenging situation the visual system has been placed in.

Amplitude:

Applicant has derived a unique measure using the present invention that can assess information loss associated with the second flash of the double-flash condition. The calculation is as follows: integral of P2 component from double-flash condition (absolute value of the amplitude 100 to 300 ms post flash)/integral of P2 waveform from the single-flash condition (absolute value of the amplitude 100 to 300 ms post flash).

The result is a percent retention value associated with the second of two flashes in the double-flash condition. Remember, the energy/information that should be there in the P2 component from the single-flash condition is known and that measure of energy/information can be taken to determine what percentage of the second flash's information actually makes it through once the visual system has been challenged by the first flash.

By way of further description, the importance of the present invention cannot be overstated. First, the neuropathological changes described above are the first to occur in the cognitive disease process-a time at which neither CSF nor brain scans are able to detect the disease, limiting the potential for early treatment. Second, the present invention doesn't assume the amyloid beta hypothesis and, therefore, may prove to be a more valid marker aMC/AD related pathology than current the gold standards. If true, the cognitive impairment detection system using the FVEP procedure would become a welcomed addition to a broader clinical assessment in the offices of neurologists and primary care physicians and would likely be the "go-to" for pharmaceutical companies and researchers that are exploring novel treatments for aMCI and AD.

Despite the promising findings associated with the more traditional method of evoking the P2, which involves the presentation of a single flash, research conducted with the present invention suggests that a double-stimulation (flash) condition produces even greater separation between those suffering from aMCI and AD and age equivalent controls. It appears to the inventor that this occurs because the first of two flashes serve as a challenge to the ascending cholinergic system and patients diagnosed with either aMCI or AD recover more slowly, producing an additional delay in the P2 latency. The interstimulus intervals examined have ranged from 10 to 120 ms, with those conditions employing 80 ms and higher producing the most favorable results. An ISI of 80 ms appears to be a threshold where the response to successive stimuli become muddled. Hence, double-flash conditions with ISIs greater than 80 ms would only be used (e.g., 370 ms ISI).

The description of the present embodiments of the invention has been presented for purposes of illustration, but is not intended to be exhaustive or to limit the invention to the form disclosed. Many modifications and variations will be apparent to those of ordinary skill in the art. As such, while the present invention has been disclosed in connection with an embodiment thereof, it should be understood that other embodiments may fall within the spirit and scope of the invention as defined by the following claims.

What is claimed is:

1. A multi-use electroencephalogram (EEG) system comprising:
  a. a strobe where the strobe is adjustable to produce a single strobe flash then multiple strobe flashes;
  b. an EEG device configured for time-locking an EEG recording with the strobe where said EEG device measures patient flash visual evoked potential (FVEP) response to the single strobe f lash and the multiple strobe flashes; and
  c. a controller connected with said strobe and said EEG device wherein said controller operates said strobe to produce one single strobe flash condition followed by a double strobe flash condition employing various interstimulus intervals in a complete counterbalanced order.

2. The system of claim 1 wherein the strobe is configured in a goggle with two lenses with more than one light emitting diode in each lens.

3. The system of claim 1 wherein the controller operates said strobe to produce the one single strobe flash condition followed by more than one of the double strobe flash condition in a complete counterbalanced order.

4. The system of claim 3 wherein the double strobe flash condition are produced with varying interstimulus intervals, durations, intensities, colors, and frequencies.

5. The system of claim 3 wherein the strobe produces the one single strobe flash condition and the double strobe flash condition selected from a group of strobe flashes consisting of: colored strobe flashes, strobe flashes of variable duration, strobe flashes of variable brightness, strobe flashes of variable frequency, and double strobe flashes of variable interstimulus intervals.

6. A multi-use electroencephalogram (EEG) system comprising:
   a. a strobe where the strobe produces a single strobe flash then multiple double strobe flashes of various durations, intensities, colors, and frequencies;
   b. a multi-use EEG acquisition system configured for recording both a continuous EEG and a time-locked EEG, including flash visual evoked potential (FVEP) and event-related potentials;
   c. a multi-use EEG analysis system, connected with the multi-use acquisition system, configured for analyzing both the continuous EEG and the time-locked EEG, including the FVEP and the event-related potentials wherein the multi-use EEG analysis system is configured for connection with a computer enabling uploading of recordings and downloading of descriptive reports.

7. The system of claim 6, wherein the strobe is configured in a goggle with two lenses with more than one light emitting diode in each lens.

8. The system of claim 6, wherein the multi-use EEG acquisition system operates said strobe to produce one single strobe flash condition followed by more than one double strobe flash condition in a complete counterbalanced order.

9. The system of claim 8, wherein the more than one double strobe flash condition is produced with varying interstimulus intervals, durations, intensities, colors, and frequencies.

10. The system of claim 6, wherein the strobe produces the single strobe flash and the double strobe flashes selected from a group of strobe flashes consisting of: colored strobe flashes, strobe flashes of variable duration, strobe flashes of variable brightness, strobe flashes of variable frequency, and double strobe flashes of variable interstimulus intervals.

11. A multi-use electroencephalogram (EEG) method consisting of:
   a. providing a strobe where the strobe is adjustable to produce a single strobe flash then multiple strobe flashes; an electroencephalogram (EEG) device configured for time-locking with the strobe where said EEG device measures patient flash visual evoked potential (FVEP) response to the single strobe flash and the multiple strobe flashes and a controller connected with said strobe and said EEG device wherein said controller operates said strobe to produce one single strobe flash condition followed by one double strobe flash condition; and
   b. activating the controller to operate the strobe such that the EEG device obtains the FVEP responses.

12. The method of claim 11 wherein the strobe is configured in a goggle with two lenses with more than one light emitting diode in each lens.

13. The method of claim 11 wherein the controller operates said strobe to produce the one single strobe flash condition followed by the one double strobe flash condition in a complete counterbalanced order.

14. The method of claim 11 wherein the controller operates said strobe to produce the one single strobe flash condition followed by more than one of the one double strobe flash condition in a complete counterbalanced order.

15. The method of claim 14 wherein the more than one of the one double strobe flash conditions are produced with varying interstimulus intervals, durations, intensities, colors, and frequencies.

16. The method of claim 11 wherein the strobe produces double flashes with varying time intervals.

17. The method of claim 16 wherein the varying time intervals are in a range from 80 ms to 500 ms.

18. The method of claim 11 wherein the strobe produces the single strobe flash and the multiple strobe flashes selected from a group of strobe flashes consisting of: colored strobe flashes, strobe flashes of variable duration, strobe flashes of variable brightness, strobe flashes of variable frequency, and double strobe flashes of variable interstimulus intervals.

* * * * *